(12) United States Patent
Hunley et al.

(10) Patent No.: US 11,116,927 B2
(45) Date of Patent: Sep. 14, 2021

(54) RESPIRATORY MASK LINER

(71) Applicants: Robert D. Hunley, Shrewsbury, PA (US); Gregory Hiemenz, Silver Spring, MD (US)

(72) Inventors: Robert D. Hunley, Shrewsbury, PA (US); Gregory Hiemenz, Silver Spring, MD (US)

(73) Assignee: Wakewell LLC, Calverton, MD (US)

( * ) Notice: Subject to any disclaimer, the term of this patent is extended or adjusted under 35 U.S.C. 154(b) by 292 days.

(21) Appl. No.: 15/675,467

(22) Filed: Aug. 11, 2017

(65) Prior Publication Data

US 2018/0043120 A1 Feb. 15, 2018

Related U.S. Application Data

(60) Provisional application No. 62/374,945, filed on Aug. 15, 2016.

(51) Int. Cl.
*A61M 16/06* (2006.01)
*A61B 5/097* (2006.01)
*D03D 3/02* (2006.01)

(52) U.S. Cl.
CPC ............ *A61M 16/06* (2013.01); *A61B 5/097* (2013.01); *D03D 3/02* (2013.01);
(Continued)

(58) Field of Classification Search
CPC ......... A61M 16/06; A61B 5/097; D03D 3/02; D03D 3/00; D03D 3/08; Y10T 442/413
See application file for complete search history.

(56) References Cited

U.S. PATENT DOCUMENTS 2,688,862 A * 9/1954 Carmen Rizzo ......... D04B 9/32
66/135
4,180,065 A * 12/1979 Bowen .................... A61F 13/08
2/239

(Continued)

OTHER PUBLICATIONS

Y.E. El Mogahzy, Engineering Textiles: Integrating the Design and Manufacture of Textile Products, 2009, Elsevier Science and Technology, 2nd Edition, pp. 208-239. (Year: 2009).*

(Continued)

*Primary Examiner* — Jan Christopher L Merene
*Assistant Examiner* — Thomas W Greig
(74) *Attorney, Agent, or Firm* — Royal W. Craig; Gordon Feinblatt LLC

(57) ABSTRACT

A replaceable liner, for a respiratory mask comprising an elastic substantially tubular shaped body dimensioned to stretch around the mask cushion. The liner is made of a knitted fabric in radially-continuous tubular structure that is preferentially formed through a circular knit to create a seamless tube. The ends of the fabric tube may be hemmed, finished with a fabric or elastic welt, or otherwise finished to prevent unraveling of the knit. The seamless tubular body may be knitted from a variety of natural yarns, such as wool or cotton, or from synthetic yarns, such as nylon, polyester, spandex, or elastic, to achieve a balance of comfort and wicking of skin oils and moisture, while maintaining sufficient radial elasticity to stretch around the respiratory mask. The fabric may be treated with antimicrobial coatings to provide protection against bacteria, fungus and reduce propensity of odors/stains.

24 Claims, 3 Drawing Sheets

(52) U.S. Cl.
CPC .............. *A61M 2205/0205* (2013.01); *A61M 2205/0216* (2013.01); *A61M 2209/00* (2013.01)

(56) References Cited

U.S. PATENT DOCUMENTS

| | | | |
|---|---|---|---|
| 5,413,149 A | | 5/1995 | Ford et al. |
| 6,287,168 B1* | | 9/2001 | Rabinowicz ......... A41C 3/0007 450/156 |
| 6,698,427 B1* | | 3/2004 | Clowers ................ A61M 16/06 128/200.24 |
| 7,472,703 B2 | | 1/2009 | Hernandez et al. |
| 7,798,155 B2* | | 9/2010 | Schweers ................ A42C 5/00 132/273 |
| 8,365,733 B2 | | 2/2013 | Rutan |
| 9,113,667 B2 | | 8/2015 | Rutan |
| 10,357,626 B1* | | 7/2019 | Baker ................. A61M 16/105 |
| 2006/0081251 A1* | | 4/2006 | Hernandez ............ A61M 16/06 128/206.21 |
| 2009/0139525 A1 | | 6/2009 | Schirm |
| 2011/0209701 A1 | | 9/2011 | Derringer et al. |
| 2013/0133856 A1* | | 5/2013 | D'Herbecourt ........ C08G 69/40 165/46 |
| 2014/0209098 A1* | | 7/2014 | Dunn ................ A61M 16/0683 128/206.21 |
| 2016/0213872 A1* | | 7/2016 | Paulk ................ A61M 16/0875 |
| 2019/0290874 A1* | | 9/2019 | Baker ................ A61M 16/0057 |

OTHER PUBLICATIONS

Lili Du, Head-and-Face Anthropometric Survey of Chinese Workers, 2008, Oxford University Press, pp. 773-782 (Year: 2008).*

* cited by examiner

RESPIRATORY MASK LINER

CROSS REFERENCE TO RELATED APPLICATION(S)

The present application derives priority from U.S. provisional application No. 62/374,945 filed 15 Aug. 2016.

BACKGROUND OF THE INVENTION

Field of the Invention

The present invention relates to a replaceable interface for use with a respiratory mask, such as a mask for administering positive airway pressure.

Description of the Background

Obstructive sleep apnea (OSA) is a common medical condition that is characterized by repetitive collapse of the upper airway during sleep, fragmented sleep and impairment of ventilation (increasing blood levels of carbon dioxide and decreasing levels of oxygen). Untreated OSA may have significant consequences and adverse clinical outcomes, including excessive fatigue, metabolic dysfunction, high blood pressure, increased risk of cardiovascular disease, and death.

Positive airway pressure therapy is one of the most common treatments for adults with OSA. Continuous positive airway pressure (CPAP) maintains a positive pharyngeal transmural pressure so that the intraluminal pressure exceeds the surrounding pressure, while also increasing end-expiratory lung volume. By doing so, CPAP stabilizes the upper airway, ensuring that it maintains patency. Positive pressure air is typically delivered through a hose and mask fitted to the face.

The prevalence of OSA associated with accompanying daytime sleepiness is approximately 3-7% for adult men and 2-5% for adult women in the general population. However, despite high quality evidence that positive airway pressure therapy reduces adverse consequences and clinical outcomes of OSA, a high percentage of patients are non-adherent—with a majority of users discontinuing use due to discomfort and air leaks. CPAP respiratory masks are typically made of plastic, such as polycarbonate or acrylonitrile butadiene styrene (ABS), and have a soft cushion to interface with the user's face. The soft cushion is often made of elastomeric materials, such as silicone, rubber, urethane, or vinyl, or of a synthetic fabric. When in contact with skin for prolonged periods, these materials can block pores and cause sweating—resulting in skin irritation and/or infection. Moreover, when high pressures are supplied, the mask interfaces tend to "burp" and leak air, which not only reduces CPAP effectiveness, but also can awaken the user or others within the vicinity of the user. Tightening of the mask straps to prevent these leaks/burps tends to exacerbate the issues of skin irritation and leads to pressure marks on the face as well as further discomfort. What is needed is a more comfortable and more effective CPAP mask, or alternatively a way to make existing CPAP masks more comfortable and effective. These needs have prompted several attempts.

For example, the Naturs Design, Inc. RemZzzs® CPAP mask liner is a doughnut-shaped pad made of 100% breathable cotton knit, and is shaped to fit the area of a patient's face which comes in direct contact with a respiratory and/or CPAP mask; including bony bridge of nose, forehead, and cheeks.

U.S. Pat. No. 8,365,733 to Rutan (Naturs Design, Inc.) issued Feb. 5, 2013 shows a liner for use with a CPAP mask including a body constructed from an absorbent material. The liner is "releasably held" by the mask and a user's face such that the outer edge extends beyond the face-engaging portion.

U.S. Pat. No. 9,113,667 to Rutan (Naturs Design) issued Aug. 25, 2015 covers an embodiment of the RemZzzs® CPAP mask liner, where the liner includes a body constructed from an absorbent material, the body having a first set of apertures and a second set of apertures spaced from the first set of apertures (see FIGS. 11-13 and explanation). The first set of apertures receives the nasal pillows and the second set of apertures is aligned with the nasal pillows when the liner is in a folded configuration.

United States Patent Application 20090139525 by Schirm, Louis published Jun. 4, 2009 shows a mask liner of soft material, preferably moleskin or the like to avoid latex-induced skin rash in mask users. The liner is apparently a doughnut-shaped pad that adheres to the mask.

U.S. Pat. No. 7,472,703 to Hernandez et al. (Innomed Technologies, Inc.) issued Jan. 6, 2009 shows a ventilation comfort interface in which a soft material is "replaceably coupled" between the interface and a user's face to alleviate discomfort.

United States Patent Application 20110209701 by Derringer et al. published Sep. 1, 2011 shows a nose pad for a CPAP mask that is adhered thereto by temporary adhesive.

Adhesive liners as above are partial solutions, but the temporary adhesives used introduce other problems, require FDA approval, often leave a residue on the mask, and do not always provide sufficient temporary fixation.

The CPAP Comfort Cover® is a flat-knit cotton/polyester blend fabric cover with an elastic band sewn around the perimeter of the fabric. This avoids the need for adhesive, but it does not conform to the inside of the mask, instead covering the orifice with a flap having a small dime-sized hole to breathe through. This restricts breathing, and the elastic inseams create bunching of the fabric around the mask which contributes to leaks and discomfort.

It would be greatly advantageous to provide an adhesive-free CPAP mask liner with all the same advantages. "Positive-pressure respiratory mask" and "CPAP mask" are herein defined as a respiratory mask configured to cover a patient's nose and/or mouth and having a recessed substantially triangular shape with edges defining a nasal bridge at the apex and an expanded bridge at the base, and an elastomeric ring surrounding the edges.

Circular knitting is well-known. For example, U.S. Pat. No. 5,413,149 to Ford et al. (Bentley-Harris Manufacturing Company) issued May 9, 1995 shows a circular-knitted fabric product for protecting and/or covering elongate substrates, such as cables, conduits, wiring and the like.

The present inventors have developed a reusable/launderable respiratory mask liner by a circular knitting process that can be fixedly yet temporarily attached to a CPAP mask without adhesives, or other respiratory PAP masks such as APAP, BiPAP, etc.

SUMMARY OF THE INVENTION

The present invention includes a replaceable interface, or liner, for the CPAP mask cushion. The first aspect of the invention is of a substantially tubular shaped liner that will stretch around the mask cushion. The liner is made of a knitted fabric in radially-continuous tubular structure that is preferentially formed through a circular knit to create a seamless tube. The ends of the fabric tube may be hemmed, finished with a fabric or elastic welt, or otherwise finished to prevent unraveling of the knit.

The fabric liner may knitted from natural yarns, such as wool or cotton, or from synthetic yarns, such as nylon, polyester, spandex, or elastic, to achieve a balance of comfort and wicking of skin oils and moisture, while maintaining sufficient radial elasticity to stretch around the respiratory mask.

The fabric may be treated with antimicrobial coatings to provide protection against bacteria, fungus and reduce propensity of odors/stains.

DETAILED DESCRIPTION

The present invention is a reusable and replaceable liner 10 for respiratory masks 20 that is substantially tubular in structure. The liner 10 is made of a knitted fabric in radially-continuous tubular structure that is preferentially formed through a circular knitting process to create a seamless tube.

Figure 1:
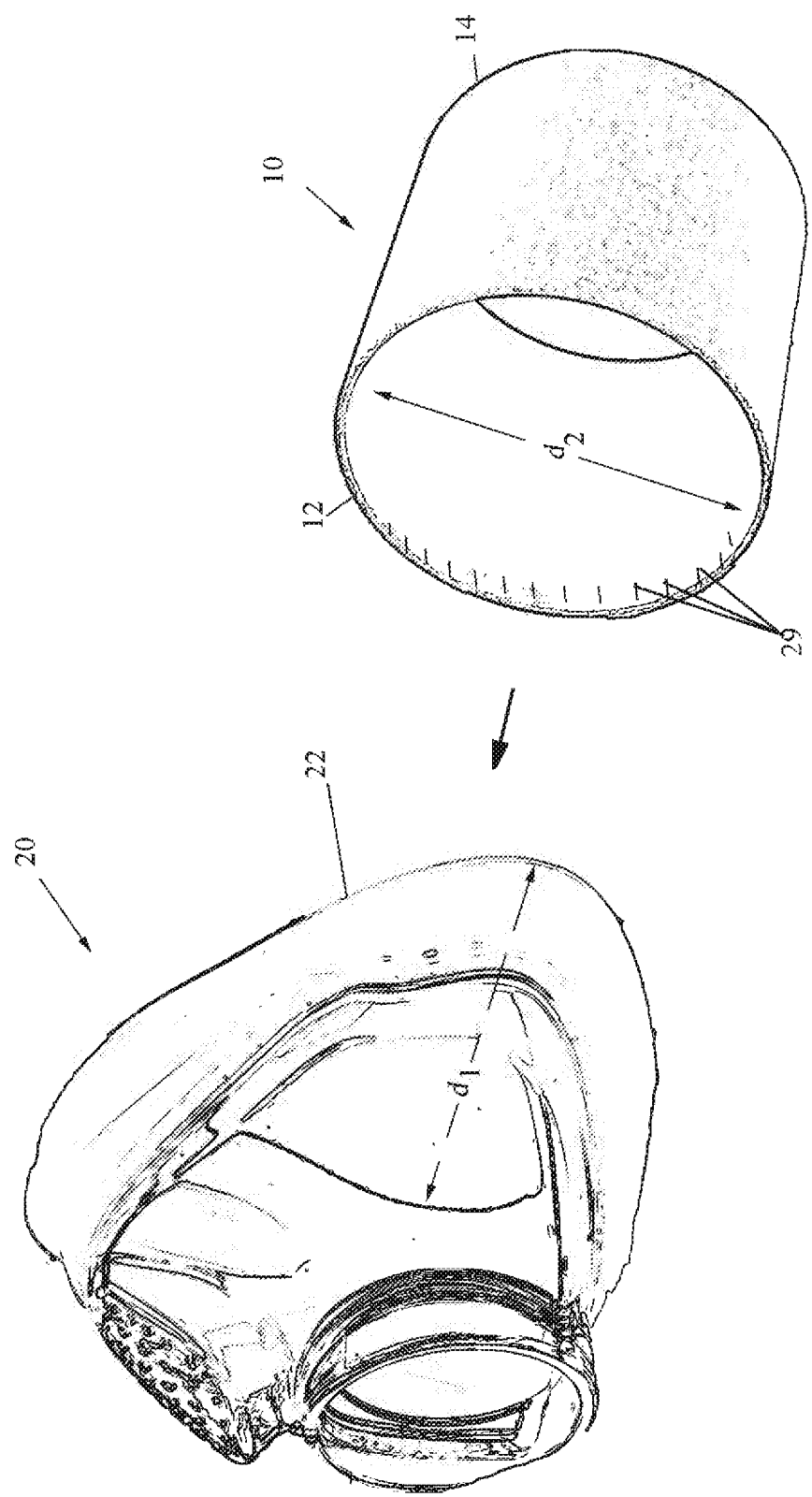
FIG. 1 is a perspective view of the invention prior to adornment on the respiratory mask—a substantially tubular fabric liner that is seamless around the radial perimeter.

Referring now more particularly to the drawings, the finished liner 10 of the present invention, prior to application to a mask 20, is represented generally in FIG. 1 and, as shown there, comprises a knitted cylindrical tube of a circular knit construction, with optional circumferential welts 12, 14 extending in a coursewise direction. Thus, the fabric construction is such that the coursewise direction of the knit fabric is generally circumferential of the annular mask cushion 22 surrounding the orifice of the mask 20.

The term "knit" or "knitted" is herein defined as a fabric created by forming a series of interconnecting loops that are able to lengthen or widen in reaction to stress. Knitted fabrics stretch more easily than wovens.

The liner 10 is fabricated slightly smaller than the mask 20 cushion 22, yet with a degree of circumferential elasticity to be so as to be stretchable over mask 20 and thereby conform closely to the annular cushion 22 of the mask 20. As best seen in FIG. 1, the liner 10 is of a single-ply circularly-knitted construction for economical conservation of materials, with optional two-ply annular welts 12, 14 sewn over the outer axial ends of the liner 10 to form a finished edge. As an alternative to welts 12, 14 the ends of the liner 10 may be hemmed, or otherwise finished to prevent unraveling of the knit.

More specifically, each liner 10 is of a suitable axial length to double over around the annular cushion 22 of the mask 20 and cling thereto, e.g., total unstretched length being within a preferred range of 1-3" and most preferably 1.5-2.5". The optional welts 12, 14 occupy less than approximately a half-inch of the overall liner 10 length.

In order to be a seamless fabric tube, the liner 10 is preferentially constructed using a circular knit via cylinder knitting machine. The absence of a seam on the radial perimeter of seamless fabric liner 10 reduces risk of leakage where the seam would otherwise interface the mask and/or the face. A secondary benefit of the circular knit is that, combined with proper yarn/thread materials, can yield a tube that is highly elastic in the radial direction. The predominant length of the liner 10 body portion may be weft knitted on a circular knitting machine and in which yarn/thread is taken into a needle during each rotation of the cylinder, resulting in a cylindrical tube. A suitable narrow tube circular knitting machine may be used, such as the Tompkins® Model R for 3"-7" diameter tubes.

In its unadorned/unstretched state, the liner 10 will have a tubular diameter $d_2$ that is slightly smaller than the effective mean outer diameter $d_1$ of the mask cushion 22 over which it will fit. Preferably the total unstretched circumference of the tubular liner 10 is within a preferred range of 2-8" and most preferably 3-8", yielding a stretched circumference ranging from 4-16".

Figure 3:
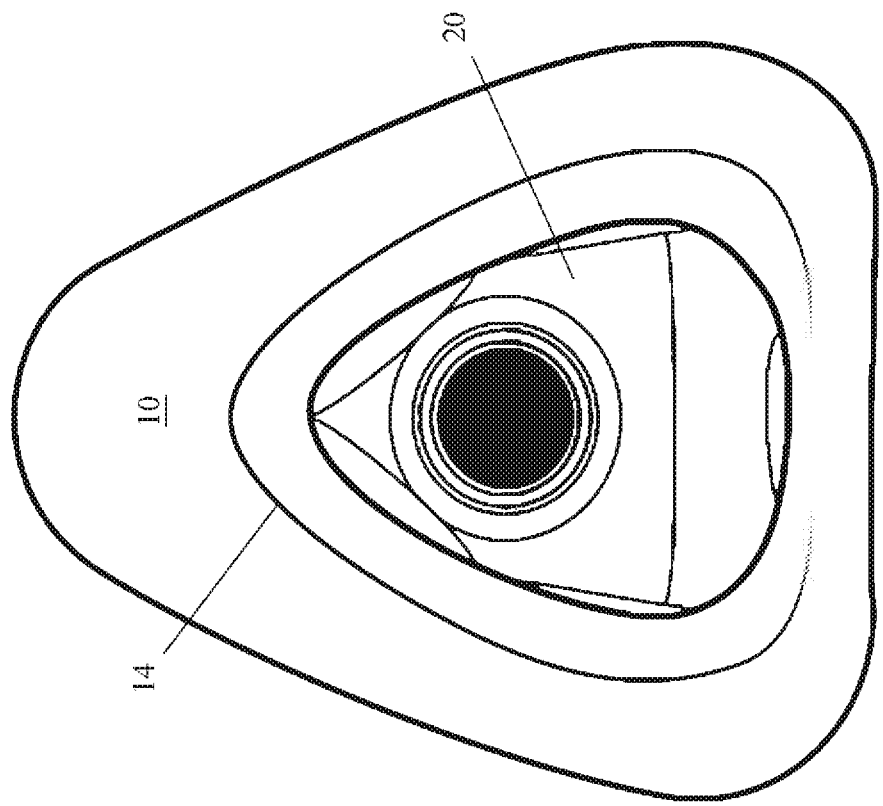
FIG. 3 is a rear view of the respiratory mask liner stretched over mask cushion.
Figure 2:
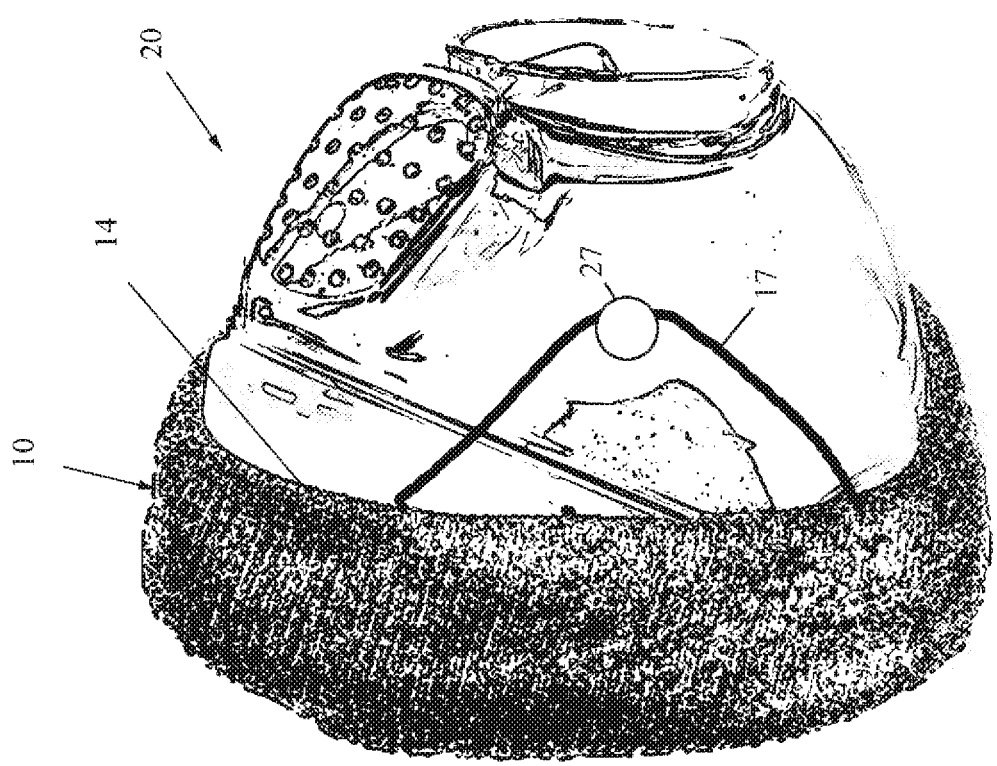
FIG. 2 is a perspective side view of a typical respiratory mask with mask liner stretched over mask cushion.
Figure 4:
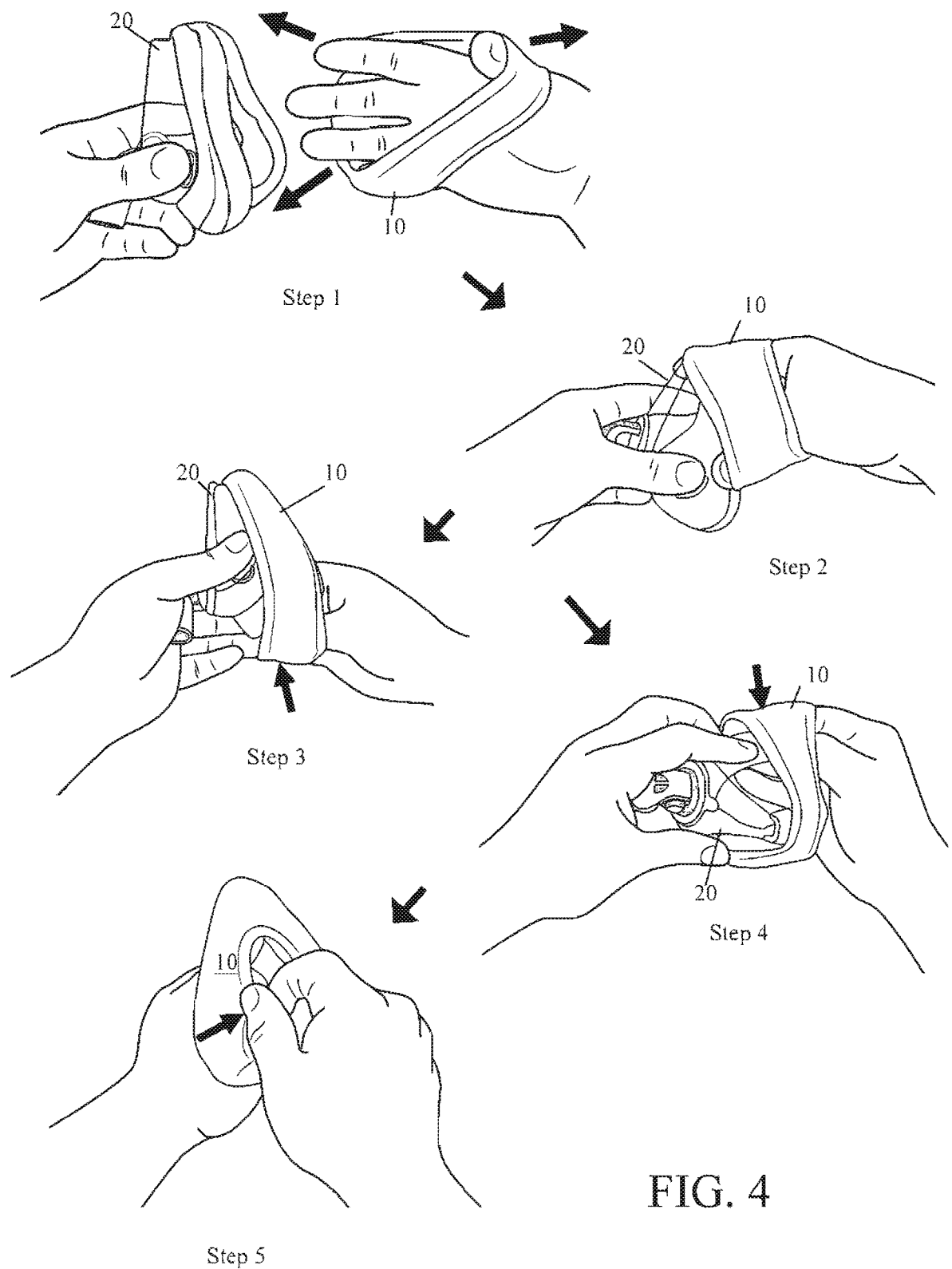
FIG. 4 is a sequential illustration for deployment on the mask.

To deploy it on the mask 20, as shown in the sequential illustration of FIG. 4, at step 1 the liner 10 is stretched open by sliding one hand through liner 10 and using the fingers to spread the liner 10 open. At step 2 one end of the stretched liner 10 is inserted over the mask cushion 22 so as to hook upper outer edge of liner 10 over top of the mask 20. At step 3 the liner 10 is stretched completely around the mask cushion 22. At step 4 the liner 10 is secured over all three rounded corners of the mask 20. At step 5 the free end of the liner 10 is released and tucked inside the mask cushion 22 such that liner 10 is doubled over the mask 20 cushion 22 and completely covers the interface. Any bunching is removed by minor tugging adjustments to ultimately provide a seamless interface with the user as shown in FIG. 2-3, circumferentially stretchable liner 10, due to the circular knitting process, fits snugly over the mask 20 cushion 22, both inside and out, without the material bunching up or wrinkling, as would be the case for any a flat knit textile with elastic hemmed in (such as the CPAP Comfort Cover®). The absence of a material bunching/wrinkling at the interfaces of the mask 20 and face reduces risk of leakage and enhances comfort.

The liner 10 may be knitted with a variety of yarn/thread types, to include natural materials (such as wool or cotton) as well as synthetics (such as polyester, nylon, spandex, or elastic), or combinations thereof. In particular, wool and some synthetic materials combine higher air permeability with improved wicking, and are advantageous for the purposes of airflow and wicking moisture/oils from the skin to improve comfort. The liner 10 elongation % in the radial directions of the fabric is a function of the fabric density, knit and materials used. Some elastic synthetic materials may also be preferred, such as spandex, to achieve desired radial elasticity, while others such as filamentary hydrophilic polyester (e.g. Sorbtek™, or the like) may be preferred for moisture wicking and soil release properties. A preferred fabric for liner 10 is a circular knit blend within a range of from 20 to 100 denier, single spun Sorbtek™, and 20-100 denier spandex, and most preferably a 20 denier single spun Sorbtek™ and 20 denier spandex blend. The circular knitting process of such a blend yields a liner 10 with consistent radial elasticity along its axial length such that it fits snugly over the mask 20 cushion 22, both inside and out, without the material bunching up or wrinkling.

Finally, the circular knit design of the preferred embodiment is inherently very durable, maintaining its material properties over time—including elasticity. Consequently, the present invention will endure repeated washing and heavy usage before requiring replacement.

In an embodiment, the liner 10 includes one or more retention features are provided for preventing the mask liner 10 from slipping off the respiratory mask 20. In a preferred embodiment, the retention feature consists of rubber applied to the inner surface of one or both welts 12, 14 to help grip the mask 20. FIG. 1 shows exemplary axial rubber segments applied to the interior of welt 12 for grip coating. Other patterns are possible, and a suitable rubber grip coating may be applied by screen printing, by extruding liquid rubber through a nozzle, or by simply adhering premanufactured rubber tape. Applying silicone or silicone-like materials, in particular, gives the unique ability to provide a mild-adhesiveness and anti-slip and release property. In an alternate embodiment, a fastener is provided for preventing the mask liner 10 from slipping off the respiratory mask 10. The fastener may, for example, be a plurality of tethers 17 each attached at both ends to the liner 10 and stretchable about a complimentary feature on the respiratory mask 20, such as raised posts 27, to secure the liner 10 thereto. Of course, one skilled in the art will readily understand that other suitable fasteners exist such as hook-and-loop fasteners, snaps, buttons, etc., all considered within the scope and spirit of the invention.

In an embodiment, the liner 10 is preferentially treated with antimicrobial treatment to provide protection against bacteria, fungus, odors, and stains—all of which can negatively affect comfort.

The presence of the liner 10 has been shown to significantly improve comfort through less irritation, less sweating, and lessened pressure marks. Moreover, the more forgiving skin interface has been shown to reduce leakage/burping around the mask perimeter—thus improving CPAP effectiveness and reducing noise and discomfort associated with its usage.

Having now set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

We claim:

1. A respiratory mask liner configured to be stretch-fit around a peripheral mask cushion of an existing positive-pressure respiratory mask and cling snugly thereto, consisting of a knitted elastic fabric body formed in a radially-continuous seamless tube, the knitted elastic fabric body being formed of a plurality of circularly-knitted interwoven fiber rows collectively forming said seamless tube and having a radial stretch characteristic that is a function of knit density or fiber composition, thereby establishing a first circumference in an unstretched state along substantially an entire length of said seamless tube within a range of from 2-8" and elastically-stretchable to a second circumference along substantially an entire length of said seamless tube of at least twice said first circumference, the respiratory mask liner being knitted by a circular knitting process to create said seamless radially-stretchable tube.

2. The respiratory mask liner according to claim 1, wherein said knitted elastic fabric body is formed in a radially-continuous seamless tube having at least one circumferential welt at one end of said continuous seamless tube.

3. The respiratory mask liner according to claim 2, wherein said knitted elastic fabric body is formed in a radially-continuous seamless tube having two circumferential welts at opposing ends of said continuous seamless tube.

4. The respiratory mask liner according to claim 1, wherein said plurality of circularly-knitted interwoven fiber rows have at least 100% radial elasticity.

5. The respiratory mask liner according to claim 4, wherein said plurality of circularly-knitted elastic rows are knitted with at least one wool strand.

6. The respiratory mask liner according to claim 4, wherein said plurality of circularly-knitted elastic rows are knitted with at least one cotton strand.

7. The respiratory mask liner according to claim 4, wherein said plurality of circularly-knitted elastic rows are knitted with at least one elastic strand.

8. The respiratory mask liner according to claim 4, wherein said plurality of circularly-knitted elastic rows are knitted with at least one synthetic strand.

9. A respiratory mask liner configured to be stretch-fit around a peripheral mask cushion of an existing positive-pressure respiratory mask having a substantially rounded triangular opening surrounded by said mask cushion and configured to interface a patient's face, the respiratory mask liner comprising a knitted elastic fabric body formed in a radially-continuous seamless tube, the knitted elastic fabric body being formed of a plurality of circularly-knitted interwoven fiber rows collectively forming said seamless tube and and having a radial stretch characteristic that is a function of knit density or fiber composition, thereby establishing a substantially uniform first diameter along substantially an entire length of said seamless tube that is less than the effective mean outer diameter of said mask cushion in an unstretched state and within a range of from 0.6-2.5", and elastically-radially-stretchable to a second diameter of at least twice said first.

10. The respiratory mask liner according to claim 9, wherein said knitted elastic fabric body is formed in a radially-continuous seamless tube having at least one radial welt at one end of said continuous seamless tube.

11. The respiratory mask liner according to claim 10, wherein said knitted elastic fabric body is formed in a radially-continuous seamless tube having two radial welts at opposing ends of said continuous seamless tube.

12. The respiratory mask liner according to claim 9, wherein said plurality of circularly-knitted interwoven fiber rows have a degree of circumferential elasticity.

13. The respiratory mask liner according to claim 12, wherein said plurality of circularly-knitted elastic rows are knitted with at least one wool strand.

14. The respiratory mask liner according to claim 12, wherein said plurality of circularly-knitted elastic rows are knitted with at least one cotton strand.

15. The respiratory mask liner according to claim 12, wherein said plurality of circularly-knitted elastic rows are knitted with at least one elastic strand.

16. The respiratory mask liner according to claim 12, wherein said plurality of circularly-knitted elastic rows are knitted with at least one synthetic strand.

17. The respiratory mask liner according to claim 10, wherein said seamless tube is single-ply.

18. The respiratory mask liner according to claim 17, wherein said seamless tube is single-ply and said at least one welt is two-ply doubled over said single-ply seamless tube.

19. The respiratory mask liner according to claim 9, wherein said seamless tube is knitted by a circular knitting machine with a rotating cylinder, resulting in a cylindrical tube.

20. The respiratory mask liner according to claim 9, wherein seamless tube is coated with an antimicrobial coating.

21. The respiratory mask liner according to claim 9, further comprising a non-slip coating for preventing said respiratory mask liner from slipping off said respiratory mask.

22. The respiratory mask liner according to claim 21, wherein said non-slip coating comprises rubber.

23. The respiratory mask liner according to claim 22, wherein said rubber grip is comprised of a rubber pattern applied to a portion of the inner surface of said continuous seamless tube.

24. The respiratory mask liner according to claim 23, wherein said rubber pattern comprises silicon rubber.

\* \* \* \* \*